United States Patent [19]
Newkirk et al.

[11] Patent Number: 5,921,973
[45] Date of Patent: Jul. 13, 1999

[54] NONWOVEN FABRIC USEFUL FOR PREPARING ELASTIC COMPOSITE FABRICS

[75] Inventors: David D. Newkirk; Jared A. Austin, both of Greer, S.C.

[73] Assignee: BBA Nonwoven Simpsonville, Inc., Simpsonville, S.C.

[21] Appl. No.: 08/775,274

[22] Filed: Feb. 17, 1997

Related U.S. Application Data

[63] Continuation of application No. 08/344,731, Nov. 23, 1994, abandoned.

[51] Int. Cl.⁶ ............................. A61F 13/15; B32B 3/10
[52] U.S. Cl. .................... 604/365; 604/367; 604/373; 442/328; 442/329; 442/394; 442/399
[58] Field of Search ................................ 442/328, 329, 442/394, 399; 604/385.1, 385.2, 373, 367, 370, 365, 366, 378; 428/138, 152, 198, 295.1, 297.1

[56] References Cited

U.S. PATENT DOCUMENTS

| | | |
|---|---|---|
| 3,807,917 | 4/1974 | Shimoda et al. . |
| 4,153,664 | 5/1979 | Sabee . |
| 4,223,063 | 9/1980 | Sabee . |
| 4,251,200 | 2/1981 | Parkin . |
| 4,525,407 | 6/1985 | Ness . |
| 4,634,739 | 1/1987 | Vassilatos ................................ 525/240 |
| 4,644,045 | 2/1987 | Fowells . |
| 4,717,325 | 1/1988 | Fujimura et al. . |
| 4,834,741 | 5/1989 | Sabee .................................... 604/385.2 |
| 4,839,228 | 6/1989 | Jezic et al. . |
| 4,910,064 | 3/1990 | Sabee . |
| 4,938,832 | 7/1990 | Schmalz . |
| 5,240,764 | 8/1993 | Haid et al. .............................. 428/224 |
| 5,242,436 | 9/1993 | Weil et al. . |
| 5,334,446 | 8/1994 | Quantville et al. ..................... 428/284 |

FOREIGN PATENT DOCUMENTS

| | | |
|---|---|---|
| 0394954 | 1/1990 | European Pat. Off. . |
| 394954 | 10/1990 | European Pat. Off. . |
| 445536 | 9/1991 | European Pat. Off. . |
| 516412 | 12/1992 | European Pat. Off. . |
| WO 90/10672 | of 0000 | WIPO . |

*Primary Examiner*—John G. Weiss
*Assistant Examiner*—David J. Cho
*Attorney, Agent, or Firm*—Alston & Bird LLP

[57] ABSTRACT

The invention is directed to composite elastic nonwoven fabrics and processes for producing the same. The fabric includes a layer of inelastic continuous or staple fibers formed from a blend of polyethylene and polypropylene laminated to an elastic layer. Preferably, the composition of the fibers ranges between 5 to 50 percent by weight of polypropylene with the balance made up of polyethylene. The nonelastic fibers are capable of being highly elongated upon mechanical stretching without adversely impacting fiber tie down. Accordingly, a smooth, strong, coherent fabric is obtained, which is especially well suited for incorporation into disposable absorbent articles such as diapers, training pants, incontinence briefs and feminine hygiene products.

24 Claims, 2 Drawing Sheets

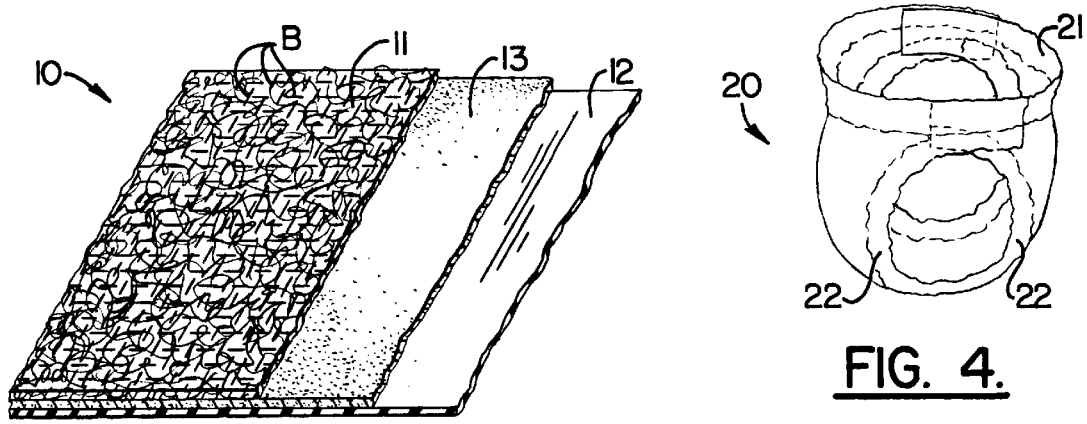
FIG. 1.
FIG. 4.
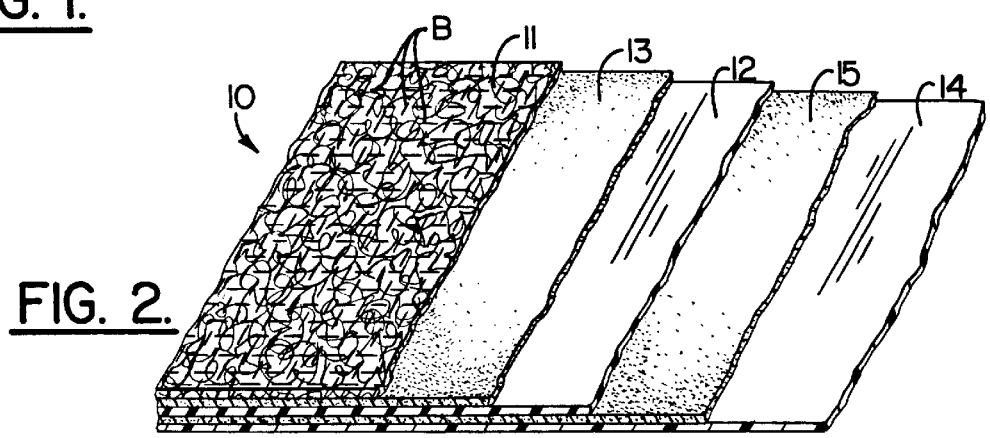
FIG. 2.
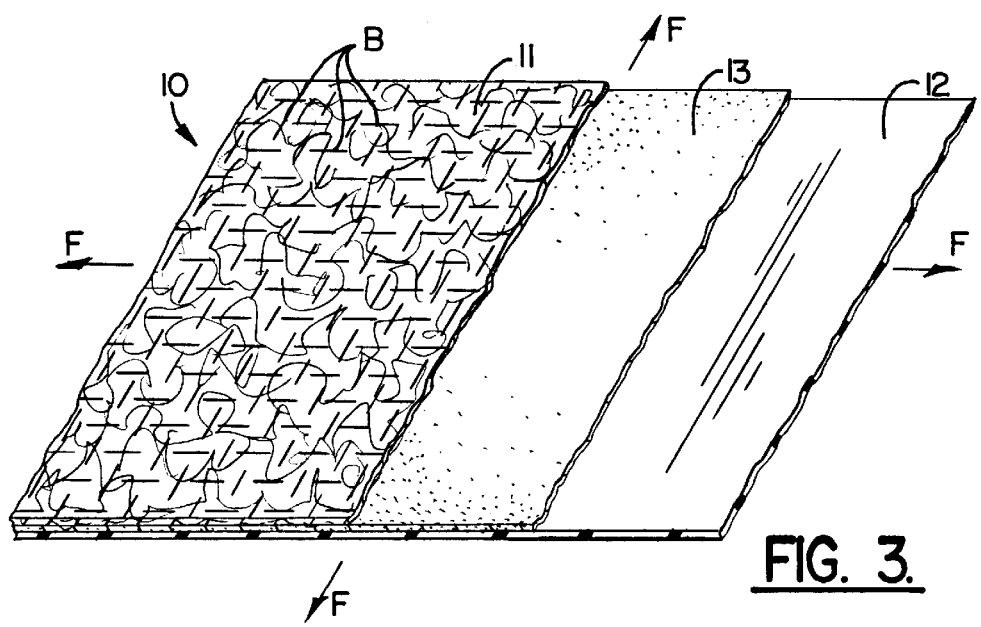
FIG. 3.

NONWOVEN FABRIC USEFUL FOR PREPARING ELASTIC COMPOSITE FABRICS

This application is a continuation of application Ser. No. 08/344,731, filed Nov. 23, 1994 now abandoned.

FIELD OF THE INVENTION

The invention relates to elastic nonwoven fabrics and processes for producing the same. More particularly, the invention relates to a nonwoven zero-strain stretch laminate comprising nonelastic fabrics capable of elongating during mechanical stretching without substantially decreasing fabric abrasion resistance.

BACKGROUND OF THE INVENTION

Nonwoven elastic composite fabrics are useful in a variety of applications such as bandaging materials, garments, diapers, supportive clothing and personal hygiene products because of their ability to conform and allow more freedom of body movement than fabrics with limited extensibility. A sizeable effort has been directed to the formation of composite nonwoven fabrics by combining elastomeric nonwoven fabrics with other fabrics. For example, composites utilizing a fibrous layer bonded to an elastic substrate have become increasingly popular, especially in disposable garment applications. Of these fabrics, "zero-strain" stretch laminates have received considerable attention. A "zero-strain" stretch laminate refers to a fabric in which at least two layers of material, one elastic, the other substantially inelastic, are secured to one another along their coextensive surfaces while in a substantially untensioned state. The fabric is subsequently subjected to mechanical stretching, thus permanently elongating the fibers. "Zero-strain" stretch lamination is advantageous in that utilizing elastic in an unstretched condition is easier and less expensive than stretched elastic used in traditional processing operations.

Fibrous webs formed of polyethylene possess properties which make them desirable for incorporation into a "zero-strain" stretch fabric. As disclosed in U.S. Pat. No. 4,644,045 to Fowells, spunbonded webs formed from low density polyethylene are particularly advantageous, possessing excellent hand, softness, and drape properties. Moreover, these fibers are capable of elongating to over 200% of their unstretched length upon mechanical stretching. Nonetheless, in spite of these advantages, elongation severely disrupts fiber tie down within the substantially inelastic component of the zero-strain laminate. As a result, the fibers detach, giving the fabric an unsightly fuzzed appearance. In addition, such detachment causes a noticeable loss in fabric strength.

SUMMARY OF THE INVENTION

The present invention overcomes these adverse effects and provides a composite nonwoven fabric with a superior combination of tensile properties and abrasion resistance. The composite fabric utilizes a nonwoven component or layer comprised of nonelastic extensible fibers formed from a blend of polyethylene and polypropylene. The fibers are capable of high elongation upon stretching without adversely impacting fiber tie down and fabric abrasion resistance. As a result, a smooth, strong, coherent composite material is obtained.

The elastic nonwoven composite fabric of the present invention includes a nonelastic layer of fibers formed from a polyethylene/polypropylene blend laminated to an elastic layer. Typically, polyethylene and polypropylene are blended in proportions such that the fibers comprise between 2 and 98 percent by weight polypropylene, balance polyethylene. Where high elasticity is of primary concern in the product, a polyethylene-rich blend is preferred. The fiber composition may range from 5 to 50 percent by weight polypropylene and 50 to 95 percent by weight polyethylene. Especially suited for applications requiring good elasticity, tensile strength and abrasion resistance are fiber compositions of from 5 to 25 percent by weight polypropylene of a melt index of 20 g/10 min. (ASTM D1238-89, 230° C.) or greater and 75 to 95 percent by weight linear low density polyethylene.

Alternatively, in applications where tensile strength is particularly important and high elasticity is of lesser concern, a polypropylene-rich blend is used. The elastic nonwoven composite fabric of this embodiment may include a nonelastic layer of fibers formed from a polyethylene/polypropylene blend where the polyethylene is present in the range of 2.5% to 10% and the polypropylene is present in the range of 90% to 97.5% by weight.

The nonelastic layer of fibers may be comprised of a staple fiber web, a spunbonded web, a meltblown web or combinations thereof. In each embodiment, the fibers are intermittently bonded together, typically by thermal point bonds, to form a strong, coherent web structure. Preferably, the intermittent bonds comprise between 6 and 30 percent of the area of the fibrous layer. The elastic layer can exist in a variety of forms including a web, an array of filaments, a foam, or a film with the most preferred being a film. The fibrous and elastic layers are laminated together by known thermal and chemical techniques with the most preferred method employing a thin continuous or discontinuous coat of stretchable adhesive.

The fabric is a "zero-strain" stretch composite in that the fibrous and elastic layers are laminated in a substantially relaxed condition. Mechanical stretching permanently elongates the fabric typically between 70 and 300 percent of its unstretched length. In accordance with the invention, the nonelastic fibers do not substantially detach from the coherent web structure as the intermittent bonds successfully secure the fibers to the elastic layer during the stretching operation. As a result, fabric fuzzing and strength loss is minimized.

In one embodiment of the invention, a second layer of polymeric material is laminated to the elastic layer on the opposite side of the outer nonelastic layer. A variety of materials can be employed in this layer, including nonwoven fabrics, laminates of carded or spunbond textile fibers and meltblown fibers, and polyolefin films such as polyethylene film. Polyethylene film is particularly suitable for use on the opposite side of the elastic layer from the nonelastic nonwoven layer.

In accordance with the invention, a desirable fabric especially well suited for incorporation into disposable absorbent articles such as diapers, training pants, incontinence briefs, and feminine hygiene products is obtained. For example, the fabric of this invention can be incorporated into the waist region of a diaper so that fit can be controlled around the baby's waist.

BRIEF DESCRIPTION OF THE DRAWINGS

Some of the features and advantages of the invention having been stated, others will become apparent from the detailed description which follows, and the accompanying drawings in which:

FIG. 1 is a schematic perspective view showing a nonwoven elastic composite fabric in an unstretched state, with the layers and bonds being exaggerated for clarity of illustration;

FIG. 2 is a perspective view showing a nonwoven elastic composite fabric similar to FIG. 1 with an additional nonelastic layer being incorporated into the material;

FIG. 3 is a perspective view showing the composite fabric of FIG. 1 being rendered elastic by mechanical stretching;

FIG. 4 is a side view of a diaper incorporating the composite fabric of this invention.

DETAILED DESCRIPTION OF A PREFERRED EMBODIMENT

Figure 5A:
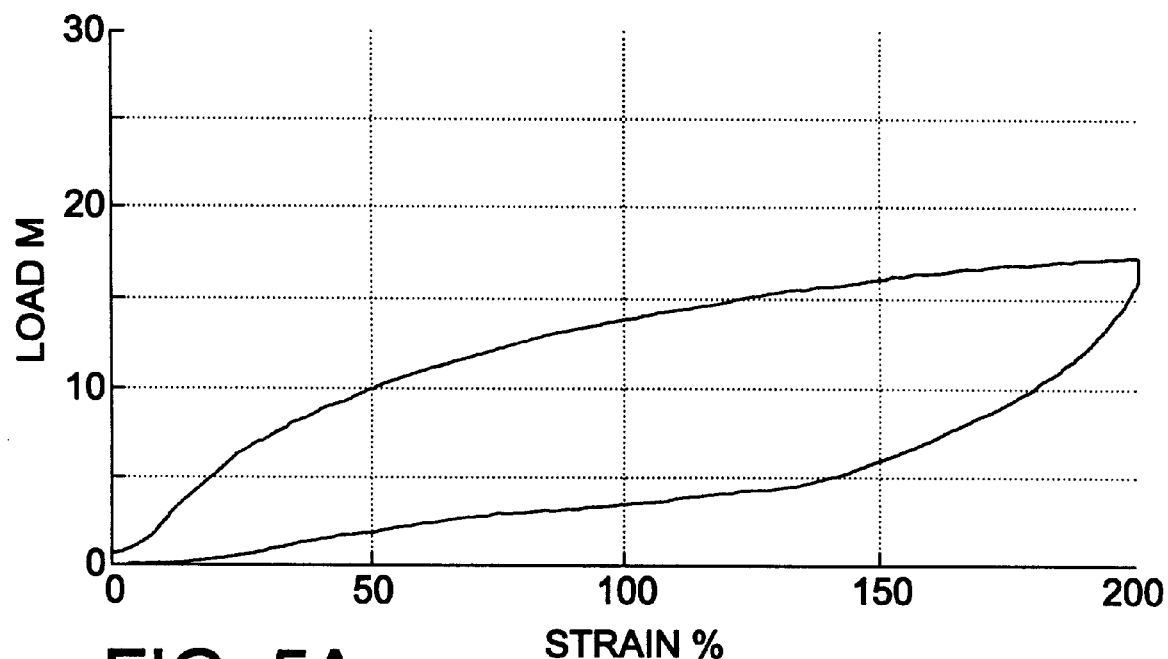
FIGS. 5A and 5B are graphs showing the stress-strain relationships of the fabric sample described in Example 2, after a first and a second elongation, respectively.

FIG. 1 shows a composite elastic nonwoven fabric in accordance with the present invention. As depicted, the composite 10 includes an extensible, nonelastic layer or web 11 of fibers laminated to an elastic layer 12. By "extensible nonelastic", it is meant that the layer or web 11 can be relatively easily stretched beyond its elastic limit and permanently elongated by application of tensile stress. In contrast, the "elastic" layer 12, when subjected to a similar amount of elongation, deforms or stretches within its elastic limit. When the tensile stress is released, the layer will recover to nearly its original length.

The nonelastic layer 11 is a nonwoven fabric or web which may be formed from various fibrous materials. More specifically, the fibers of layer 11 may suitably comprise either discrete staple fibers or continuous filaments. The nonelastic layer 11 may also be formed from a laminate of discrete staple fibers or continuous filaments and meltblown fibers.

A continuous filament nonwoven web may be produced, for example, by the conventional spunbond process wherein molten polymer is extruded into continuous filaments which are subsequently quenched, attenuated by a high velocity fluid, and collected in random arrangement on a collecting surface. After filament collection, any thermal or chemical bonding treatment may be used to form a plurality of intermittent bonds, indicated by the reference character B in FIG. 1, such that a coherent web structure results. In this regard, thermal point bonding is most preferred. Various thermal point bonding techniques are known, with the most preferred utilizing calender rolls with a point bonding pattern. Any pattern known in the art may be used with typical embodiments employing continuous or discontinuous patterns. Preferably, the bonds B cover between 6 and 30 percent of the area of the continuous layer 11, more preferably 8 to 18 percent, and most preferably, 12 percent of the layer is covered. By bonding the web in accordance with these percentage ranges, the filaments are allowed to elongate throughout the full extent of stretching while the strength and integrity of the fabric is maintained.

A staple fiber nonwoven web can be formed from any of the conventional methods known to the skilled artisan, with carding being most preferred. As known, carding is typically carried out on a machine which utilizes opposed moving beds or surfaces of fine, angled, spaced apart teeth or wires to pull clumps of staple fibers into a web. Fibers within the web are then subjected to bonding to form a coherent web structure by any suitable thermal or chemical bonding treatment. For example, thermal point bonds are formed in a manner previously described to impart strength and flexibility to the fabric.

In accordance with the invention, the staple fibers or continuous filaments which form the nonelastic layer 11 are of a blend of at least two components—a polypropylene component and a polyethylene component. The polyethylene component and the polyethylene component are immiscible and form distinct separate phases in the fibers.

Whether in staple or continuous filament form, the fibers comprise between 2 and 98 percent by weight polypropylene and 98 and 2 percent by weight polyethylene. Where a product with high elasticity is desired, a polyethylene-rich blend is preferred. The fiber composition may range from 5 to 50 percent by weight polypropylene and 95 to 50 percent by weight polyethylene, and most desirably between 5 to 25 percent by weight polypropylene and 75 to 95 percent by weight polyethylene. Especially suited for applications requiring good elasticity, tensile strength and abrasion resistance are fiber compositions of from 5 to 25 percent by weight polypropylene of a melt index of 20 g/10 min. (ASTM D1238-89, 230° C.) or greater and 75 to 95 percent by weight linear low density polyethylene. In these embodiments, the lower melting polyethylene is present as a substantially continuous phase in the blend and the higher melting polypropylene is present as a discontinuous phase dispersed in the polyethylene phase. Alternatively, in applications where tensile strength is particularly important and high elasticity is of lesser concern, a polypropylene-rich-blend is used. The elastic nonwoven composite fabric of this embodiment may include a nonelastic layer of fibers formed from a polyethylene/polypropylene blend where the polyethylene is present in the range of 2.5% to 10% and the polypropylene is present in the range of 90% to 97.5% by weight.

In producing the fibers, the polyethylene and polypropylene components are combined in appropriate proportional amounts and intimately blended before being melt-spun. In some cases sufficient mixing of the polymer components may be achieved in the extruder as the polymers are converted to the molten state, although it may be preferable to use a separate mixing step. Among the commercially well suited mixers that can be used include the Barmag 3DD three-dimensional dynamic mixer supplied by Barmag AG of Germany and the RAPRA CTM cavity-transfer mixer supplied by the Rubber and Plastics Research Association of Great Britain.

Various types of polyethylene may be employed with the most preferred being low density polyethylene. As an example, a branched (i.e., non-linear) low density polyethylene or a linear low density polyethylene (LLDPE) can be utilized and produced from any of the well known processes. LLDPE is typically produced by a catalytic solution or fluid bed process under conditions established in the art. In general, LLDPE can be produced such that various density and melt index properties are obtained which make the polymer well suited for melt-spinning with polypropylene. In particular, preferred density values range from 0.87 to 0.95 g/cc and preferred melt index values usually range from 0.1 to about 150 g/10 min. (ASTM D1238-89, 190° C.). Examples of suitable commercially available linear low density polyethylene polymers include those available from Dow Chemical Company, such as ASPUN Type 6811 (27 MI, density 0.923), Dow LLDPE 2500 (55 MI, 0.923 density), Dow LLDPE Type 6808A (36 MI, 0.940 density), and the Exact series of linear low density polyethylene polymers from Exxon Chemical Company, such as Exact 2003 (31 MI, density 0.921).

Various polypropylene polymers made by processes known to the skilled artisan may also be employed. In general, the propylene component can be an isotactic or syndiotactic polypropylene homopolymer, copolymer, or terpolymer with the most preferred being in the form of a homopolymer. For the purposes of the invention, polypropylene is preferably produced at melt index values suitable for melt spinning with polyethylene. Examples of commercially available polypropylene polymers which can be used in the present invention include SOLTEX Type 3907 (35 MFR, CR grade), HIMONT Grade X10054-12-1 (65 MFR), Exxon Type 3445 (35 MFR), Exxon Type 3635 (35 MFR) and AMOCO Type 10-7956F (35 MFR), Aristech CP 350 JPP.

Elastic layer 12 can exist in various forms including webs of bonded filaments, nets, films, foams, parallel arrays of filaments, and the like. Preferably, a film is employed. Such structures are produced by conventional methods known to the skilled artisan. As also known, any suitable elastomeric forming resins or blends thereof may be utilized in producing the above structures. Such suitable materials include the diblock and triblock copolymers based on polystyrene (S) and unsaturated or fully hydrogenated rubber blocks. The rubber blocks can consist of butadiene (B), isoprene (I), or the hydrogenated version, ethylene-butylene (EB). Thus, S-B, S-I, S-EB, as well as S-B-S, S-I-S, and S-EB-S block copolymers can be used. Preferred elastomers of this type include the KRATON polymers sold by Shell Chemical Company or the VECTOR polymers sold by DEXCO. Other elastomeric thermoplastic polymers include polyurethane elastomeric materials such as ESTANE sold by B. F. Goodrich Company; polyester elastomers such as HYTREL sold by E. I. Du Pont De Nemours Company; polyetherester elastomeric materials such as ARNITEL sold by Akzo Plastics; and polyetheramide materials such as PEBAX sold by Elf Atochem Company. Blends of these polymers with other thermoplastic polymers, such as, for example, polyolefins may be employed to enhance processing such as decreasing melt viscosity, allow for lower melt pressures and temperatures and/or increase throughput.

In accordance with the invention, the composite fabric 10 is formed by laminating nonelastic layer 11 and elastic layer 12 utilizing any of the well established thermal or chemical techniques including thermal point bonding, through air bonding, and adhesive bonding, with adhesive bonding being preferred. A suitable adhesive is applied either to fibrous layer 11, to elastic layer 12, or to both, as either a continuous or discontinuous coating, to form an adhesive layer 13. Where a continuous adhesive coating is employed, the layer 13 should be relatively thin and the adhesive should be sufficiently flexible or extensible to allow the filaments to elongate upon stretching. Where a discontinuous adhesive is employed, any intermittent pattern can be used such as, for example, lines, spirals, or spots, and the adhesive can be less extensible. The adhesive can be applied continuously or intermittently by any accepted method including spraying, slot coating, and the like.

Suitable adhesives can be made from a variety of materials including polyolefins, polyvinyl acetate polyamides, hydrocarbon resins, waxes, natural asphalts, styrenic rubbers, and blends thereof. Preferred adhesives include those manufactured by Century Adhesives, Inc. of Columbus, Ohio and marketed as Century 5227 and by H. B. Fuller Company of St. Paul, Minn. and marketed as HL-1258.

In assembling the composite fabric 10, layers 11 and 12 are provided in a relaxed state from individual supply rolls. Adhesive is then applied over the surface of elastic layer 12 or fibrous layer 11. Soon after the adhesive is applied, the layers are subjected to pressure thus forming fabric 10. For example, the layers can be fed through calender nip rolls.

In a alternative embodiment depicted in FIG. 2, a layer of nonelastic polymeric material 14 may be utilized on the side of elastic layer 12 opposite fibrous layer 11. Any suitable material may be employed in various forms such as, for example, woven or nonwoven material, films or composites, such as a film-coated nonwoven. The layer 14 of nonelastic polymeric material on the side of the elastic layer 12 opposite fibrous layer 11 may be a second fibrous layer, so that a fibrous layer 11 is used on both faces of the elastic layer 12. Typically, a thermoplastic polymer film is used with preferred polymers being polypropylene or polyethylene. Commercially desirable films includes those manufactured by Tredegar Industries, Inc. of Terre Haute, Ind. If the layer 14 is substantially impervious to liquids, it can be suitably employed as a back sheet in personal garment applications such as diapers, training pants, incontinence briefs and feminine hygiene products. Any well known techniques for laminating layer 14 to the composite structure may be utilized; preferably, layer 14 is laminated by a thin layer 15 of adhesive in a manner previously described.

Referring to FIG. 3, stretching forces are applied to composite fabric 10 imparting elasticity in the machine direction (MD) and/or cross-machine direction (CD). Numerous established techniques can be employed in carrying out this operation. For example, a common way for obtaining MD stretch is to pass the fabric through two or more sets of nip rolls, each set moving faster than the previous set. CD stretch may be achieved through tentering. Other means may be employed; for example, "ring rolling" as disclosed in U.S. Pat. No. 5,242,436 to Weil et al., incorporated herein by reference, is often used in obtaining CD and/or MD stretch.

Upon application of stretching forces (denoted by F) on fabric 10, fibers within nonelastic layer 11 oriented in the direction of the stretching forces experience tension and the fabric and fibers undergo deformation. During this process, the fibers are capable of elongating well beyond their unstretched length. As an example, fabric elongation between 70 and 300 percent is often realized. In most instances, the fibers are stretched past their elastic limit and become permanently extended. In accordance with the invention, intermittent bonds B distributed throughout nonelastic layer 11 are of high strength such that fibers are sufficiently tied down within the nonelastic layer 11 that fiber detachment is minimized during the elongation process. The heightened bond strength can be attributed to the polypropylene in the blended fibers. Accordingly, fiber detachment is reduced with the desirable result that abrasion resistance is maintained and fuzzing is minimized. Moreover, fabric strength is maintained as the coherent web structure is kept in tact during the stretching operation.

The fabric 10 is particularly well suited for use in various disposable garments such as diapers, training pants, incontinence briefs and feminine hygiene products. The fabric may be utilized in a diaper, such as the one illustrated in FIG. 4 (denoted as 20) having a waist region 21 and leg cuff components 22. The composite fabric may be typically incorporated into the waist region 21 of the diaper as a pair of side panels that become elastic upon mechanical stretching as described above. As taught for example in detail in U.S. Pat. No. 5,196,000, the resulting pair of elastic side panels provide a more comfortable and contouring fit of the diaper to the wearer and sustain that fit. The pair of elastic side panels made from composite fabric 10 develop and maintain the tensions generated by fastening the tape closure system. Moreover, since the composite fabric 10 is both soft and strong, the diaper can withstand rigorous movement of the wearer without rubbing or chafing the wearer's skin during use.

The following examples serve to illustrate the invention but are not intended to be limitations thereon.

EXAMPLE 1

Samples of continuous filament spunbonded nonwoven webs of basis weight approximately 25 grams/square meter were produced from blends of a linear low density polyethylene with a melt flow rate of 27 (Dow 6811A LLDPE) and a polypropylene homopolymer (either Appryl 3250 YR1 or Aristech CP350J) in various blend proportions. Control fabrics of 100 percent polypropylene and 100 percent polyethylene were also produced under similar conditions. The fabrics were produced by melt spinning continuous filaments of the various polymers or polymer blends, attenuating the filaments pneumatically by a slot draw process, depositing the filaments on a collection surface to form webs, and thermally bonding the webs using a patterned calender roll with a 12 percent bond area. The tensile strength and elongation properties of these fabrics and their abrasion resistance were measured, and these properties are listed in Table 1. As shown, the 100 percent polypropylene control fabric had excellent abrasion resistance, as indicated by no measurable fuzz generation; however the fabrics had very low elongation, thus limiting the utility of such fabrics in zero-strain stretch laminates. The 100 percent polyethylene control fabric exhibited excellent elongation properties, but very poor abrasion resistance (high fuzz values) and relatively low tensile strength. Surprisingly, the fabrics made of polypropylene/polyethylene blends exhibited an excellent combination of abrasion resistance, high elongation, and good tensile strength. The high filament elongation makes the fabrics well suited for use in an elastic composite structure.

EXAMPLE 2

Figure 5B:
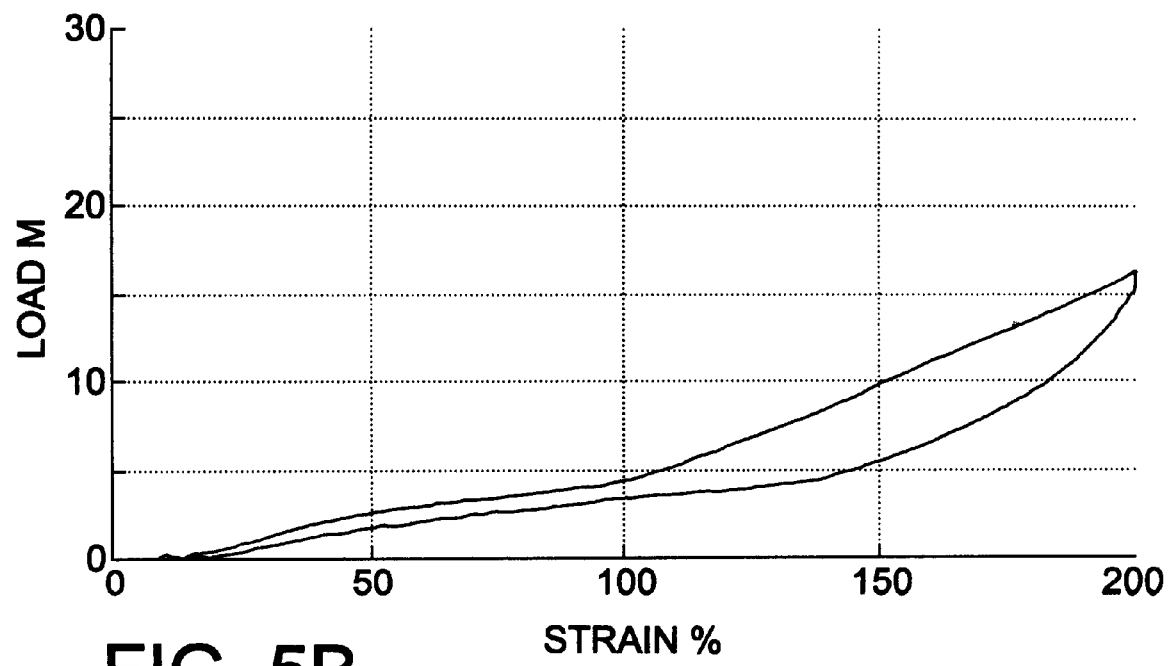

An elastic film of 1.5 mil thickness was cast from Hytrel 8122 polyester elastomer sold by E. I. Du Pont DeNemours Company. A sample of the elastic film was sprayed with an all purpose adhesive (Locktite Corporation) and was bonded by application of pressure to a 25 grams per square meter spunbonded fabric containing 15% polypropylene and 85% polyethylene (one of the nonwoven fabric samples described in Example 1). The cross machine direction of the fabric coincided with the machine direction of the film. A 1.5 inch wide sample of the resulting composite was placed in the jaws of an Instron tensile tester and elongated to 200% extension. The composite was returned to 0% extension. The resulting stress-strain curve is given in FIG. 5A. The spunbonded component remained attached to the elastic film but the filaments were elongated, so that the unextended composite had a bulky appearance. The composite was elongated a second time to 200% extension and then returned to 0% extension. The resulting stress-strain curve is given in FIG. 5B. The modulus of elasticity was much lower for the second extension, because the filaments of the spunbonded component were no longer resisting the extension. The composite had stretch behavior characteristic of an elastic material.

EXAMPLE 3

A fabric of the invention (Fabric A) was prepared by thermal point bonding three polyolefin webs placed in juxtaposition. These webs were melt spun from the following polymers:

Outer layer #1—8.5 grams per square meter 96% polypropylene (Exxon 3445)/4% polyethylene (Dow 05862N)

Middle Layer—2 grams per square meter 100% polypropylene (Exxon 3546G) meltblown fibers Outer layer #2—8.5 grams per square meter 96% polypropylene (Exxon 3445)/4% polyethylene (Dow 05862N)

The average fiber size in the outer layers was 3.3 dtex. The average fiber diameter in the middle layer was 1.9 microns. The webs were bonded using a set of calender rolls with 17% bond area. The mechanical properties of this fabric, as well as those of a control fabric made of 100% polypropylene (Fabric B) are given in Table 2. The higher elongation of the fabric containing polyethylene in the filaments of the outer layers is clearly evident.

A sample of this trilaminate fabric (Fabric A) is inserted as a barrier cuff component into a diaper of the design described in U.S. Pat. No. 4,738,677. This diaper also incorporates a fastening system as described in U.S. Pat. No. 5,242,436. In this diaper, the above polyolefin trilaminate (Fabric A) is adhesively attached to a section of elastic foam in the side panel region of the diaper. The resulting elastic laminate is subjected to 33% extension. The thermal point thermal bonds of the inelastic trilaminate component remain intact while the filaments connecting the bonds are elongated. The result is that the side panel section of the diaper becomes stretchable, the elastic foam dominating its stress-strain characteristics.

The invention has been described in considerable detail with reference to its preferred embodiments. However, it will be apparent that numerous variations and modifications can be made without departure from the spirit and scope of the invention as described in the foregoing specification and defined in the appended claims.

TABLE 1

MECHANICAL PROPERTIES OF
POLYPROPYLENE (PP)/POLYETHYLENE (PE) BLEND FABRICS

| Fabric | MD Tensile (g/cm)[1] | CD Tensile (g/cm)[1] | MD Elong (%)[1] | CD Elong (%)[1] | Fuzz (mg)[2] | Taber Abrasion (cycles-rubber wheel)[3] | Taber Abrasion (cycles-felt wheel)[3] |
|---|---|---|---|---|---|---|---|
| 100% PP | 925 | 405 | 62 | 70 | 0.0 | 40 | 733 |
| 65/35 PP/PE | 1211 | 473 | 102 | 128 | 0.6 | — | — |
| 50/50 PP/PE | 1110 | 415 | 147 | 145 | 0.3 | — | — |
| 25/75 PP/PE | 764 | 273 | 170 | 190 | 0.3 | 32 | 200 |

TABLE 1-continued

MECHANICAL PROPERTIES OF
POLYPROPYLENE (PP)/POLYETHYLENE (PE) BLEND FABRICS

| Fabric | MD Tensile (g/cm)[1] | CD Tensile (g/cm)[1] | MD Elong (%)[1] | CD Elong (%)[1] | Fuzz (mg)[2] | Taber Abrasion (cycles-rubber wheel)[3] | Taber Abrasion (cycles-felt wheel)[3] |
|---|---|---|---|---|---|---|---|
| 15/85 PP/PE | 676 | 277 | 199 | 224 | 0.5 | 22 | 500 |
| 10/90 PP/PE | 426 | 170 | 109 | 141 | 0.3 | — | — |
| 100% PE | 296 | 63 | 168 | 131 | 19.0 | 10 | 15 |

[1]Tensile and Peak Elongation were evaluated by breaking a one inch by seven inch long sample generally following ASTM D1682-64, the one-inch cut strip test. The instrument cross-head speed was set at 5 inches per minute and the gauge length was set at 5 inches per minute. The Strip Tensile Strength, reported as grams per inch, is generally the average of at least 8 measurements. Peak Elongation is the percent increase in length noted at maximum tensile strength.
[2]Fuzz is determined by repeatedly rubbing a soft elastomeric surface across the face of the fabric a constant number of times. The fiber abraded from the surface is then weighed. Fuzz is reported as mg weight observed.
[3]Conducted according to ASTM D3884-80 where the number of cycles was counted until failure. Failure was defined as the appearance of a hole of one square millimeter or greater in the surface of the fabric.

TABLE 2

MECHANICAL PROPERTIES OF TRILAMINATE FABRICS

| | FABRIC A | | | FABRIC B | | |
|---|---|---|---|---|---|---|
| | x | σ | N | x | σ | N |
| Total basis weight (gsm) | 21.052 | 1.238 | 120 | 21.2575 | 0.9125 | 96 |
| Thickness (mm) | 0.24 | 0.02 | 120 | 0.26 | 0.02 | 96 |
| Spunbond Denier (dpf) | | | | | | |
| Top | 2.9 | 0.348 | 120 | 2.9 | 0.16 | 192 |
| Bottom | 3.2 | 0.652 | 120 | 2.8 | 0.13 | 192 |
| Meltblown Dia. (microns) | 2.014 | 0.84 | 120 | 1.8825 | 0.63 | 192 |
| Tensiles (g/in) | | | | | | |
| MD | 2354.6 | 364.8 | 120 | 2700.3 | 390.3 | 96 |
| CD | 595.6 | 130.7 | 120 | 720.4 | 148.0 | 96 |
| Elongation at Max. (%) | | | | | | |
| MD | 117.1 | 19.3 | 120 | 68.1 | 11.2 | 96 |
| CD | 98.2 | 23.5 | 120 | 63.6 | 11.3 | 96 |
| Elongation at Break (%) | | | | | | |
| MD | 128.1 | 25.1 | 120 | 78.6 | 18.8 | 96 |
| CD | 128.1 | 27.4 | 120 | 95.6 | 16.8 | 96 |
| TEA (cm-g/cm2) | | | | | | |
| MD | 859.3 | 221.5 | 120 | 550.3 | 139.2 | 96 |
| CD | 185.0 | 68.2 | 120 | 143.9 | 41.8 | 96 |

What is claimed:

1. A composite nonwoven fabric comprising a nonelastic layer of fibers formed from a polymer blend comprising polypropylene and polyethylene, said nonelastic layer including a plurality of intermittent bonds bonding the fibers together to form an extensible nonelastic coherent web, a substantially continuous elastic film layer laminated to said nonelastic layer of intermittently bonded fibers, and an adhesive layer disposed between said nonelastic layer and said elastic film layer laminating the nonelastic and elastic layers together to form the composite fabric, wherein said nonelastic layer of fibers has been permanently elongated by mechanical stretching and the composite fabric exhibits elastic properties.

2. A composite nonwoven fabric according to claim 1 wherein said fibers comprise between 5 to 50 percent by weight polypropylene and 50 to 95 percent by weight polyethylene.

3. A composite nonwoven fabric according to claim 1 wherein said fibers comprise from 5 to 25 percent by weight polypropylene of a melt index of 20 g/10 min. or greater and 75 to 95 percent by weight linear low density polyethylene.

4. A composite nonwoven fabric according to claim 1 wherein said nonelastic layer of fibers has been permanently elongated between 70 and 300 percent of its original unstretched length.

5. A composite nonwoven fabric according to claim 4, wherein said fabric has a rubber wheel taber abrasion value of greater than 10 cycles.

6. A composite nonwoven fabric according to claim 1 wherein said intermittent bonds are thermal point bonds.

7. A composite nonwoven fabric according to claim 1 wherein said intermittent bonds comprise between 6 and 30 percent of the area of the nonelastic layer.

8. A composite nonwoven fabric according to claim 1 wherein said nonelastic layer of fibers comprises a thermally bonded spunbond nonwoven web of randomly arranged substantially continuous filaments.

9. A composite nonwoven fabric according to claim 1 wherein said nonelastic layer of fibers comprises a thermally bonded spunbond nonwoven web of randomly arranged substantially continuous filaments and meltblown fibers.

10. A composite nonwoven fabric according to claim 8 or 9, wherein the substantially continuous filaments of said nonelastic layer are comprised of a blend of 2.5 to 10 weight percent polyethylene and 90 to 97.5 weight percent polypropylene.

11. A composite nonwoven fabric according to claim 1 wherein said nonelastic layer of fibers comprises a thermally bonded carded web of staple fibers.

12. A composite nonwoven fabric according to claim 1 comprising an additional nonelastic layer of fibers laminated to the side of said elastic layer opposite said first-mentioned nonelastic layer, said additional nonelastic layer comprising fibers formed from a blend of polyethylene and polypropylene, said second nonelastic layer including a plurality of intermittent bonds bonding the fibers together to form a coherent web.

13. A composite nonwoven fabric according to claim 1 further comprising an outer layer of a polymeric film laminated to the side of said elastic layer opposite said nonelastic layer.

14. A composite nonwoven fabric according to claim 13 wherein said outer layer of a polymeric film comprises a polyolefin film.

15. A composite nonwoven fabric comprising a nonelastic layer of fibers formed from a polymer blend comprising polypropylene and polyethylene, said nonelastic layer including a plurality of intermittent bonds bonding the fibers together to form an extensible nonelastic coherent web, a substantially continuous elastic film layer laminated to said nonelastic layer of intermittently bonded fibers, and an adhesive layer disposed between said nonelastic layer and said elastic film layer laminating the nonelastic and elastic layers together to form the composite fabric, wherein said nonelastic layer of fibers is capable of being permanently elongated by mechanical stretching so that the composite fabric exhibits elastic properties.

16. A composite nonwoven fabric comprising an elastic layer, a spunbonded nonwoven web of randomly arranged substantially continuous filaments formed from a blend of 5 to 50 percent by weight polypropylene and 50 to 95 percent by weight polyethylene, and a multiplicity of discrete thermal point bonds bonding the continuous filaments to form an extensible nonelastic coherent web, said thermal point bonds comprising between 6 and 30 percent of the area of the spunbonded web, and an adhesive disposed between said spunbonded nonwoven web and said elastic layer to bond the spunbonded web to said elastic layer.

17. A composite nonwoven fabric according to claim 16 wherein said spunbonded web has been permanently elongated by mechanical stretching so as to extend said spunbonded web between 70 and 300 percent of its unstretched length.

18. A composite nonwoven fabric according to claim 16 comprising an additional spunbonded nonwoven web of randomly arranged substantially continuous filaments, said additional spunbonded nonwoven web being disposed on the opposite side of said elastic layer from said first-mentioned spunbonded nonwoven web and being formed from a blend of 5 to 50 percent by weight polypropylene and 50 to 95 percent by weight polyethylene, a multiplicity of discrete thermal point bonds bonding the continuous filaments of said additional spunbonded web to form an extensible nonelastic coherent web, said thermal point bonds comprising between 6 and 30 percent of the area of the spunbonded web, and an adhesive disposed between said additional spunbonded nonwoven web and said elastic layer to bond said additional spunbonded web to said elastic layer.

19. A composite nonwoven fabric comprising an elastic layer, a carded web of staple fibers formed from a blend of 5 to 50 percent by weight polypropylene and 50 to 95 percent by weight polyethylene, a multiplicity of discrete thermal point bonds bonding the staple fibers to form an extensible nonelastic coherent web, said thermal point bonds comprising between 6 and 30 percent of the area of the carded web, and an adhesive disposed between said carded web and said elastic layer to bond the carded web to said elastic layer.

20. A composite nonwoven fabric according to claim 19 wherein said carded web has been permanently elongated by mechanical stretching so as to extend said web between 70 and 300 percent of its unstretched length.

21. A composite nonwoven fabric according to claim 16 or 19 wherein said adhesive is an elastomeric adhesive and extends substantially continuously over said web.

22. A diaper having waist, side and leg cuff components, at least one of said components comprising a composite nonwoven fabric according to any one of claims 2, 16, 17, or 19.

23. A diaper having elastic panels in the waist region, said panels comprising an elastic composite fabric according to claim 1.

24. A disposable absorbent article comprising a composite nonwoven fabric according to any one of claims 1, 12, 13, 16, or 17.

* * * * *

UNITED STATES PATENT AND TRADEMARK OFFICE
CERTIFICATE OF CORRECTION

PATENT NO. : 5,921,973
DATED : July 13, 1999
INVENTOR(S) : Newkirk et al.

It is certified that error appears in the above-identified patent and that said Letters Patent is hereby corrected as shown below:

On the title page, [73] Assignee, "BBA Nonwoven Simpsonville, Inc." should read --BBA Nonwovens Simpsonville, Inc.--.

On the title page, [56] References Cited, U.S. PATENT DOCUMENTS, insert the following references:

| | | |
|---|---|---|
| --3,988,519 | 10/1976 | Stoller |
| 4,606,964 | 8/1986 | Wideman |
| 4,847,134 | 7/1989 | Fahrenkrug et al. |
| 5,503,908 | 4/1996 | Faass |
| 5,592,690 | 1/1997 | Wu |
| 5,633,070 | 5/1997 | Murayama et al. |
| 5,635,290 | 6/1997 | Stopper et al.--. |

Columns 9 - 10, table 2, line 9, needs indentation beginning with "2.9" so columns will be correct.

Column 12, line 48, "claims 2" should read --claims 1--.

Signed and Sealed this

Twenty-eighth Day of December, 1999

Attest:

Q. TODD DICKINSON

*Attesting Officer*   Acting Commissioner of Patents and Trademarks